United States Patent
Jaffe et al.

(10) Patent No.: US 12,252,423 B2
(45) Date of Patent: *Mar. 18, 2025

(54) BIODEGRADATION OF FLUOROCHEMICALS

(71) Applicant: The Trustees of Princeton University, Princeton, NJ (US)

(72) Inventors: Peter R. Jaffe, Princeton, NJ (US); Shan Huang, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 1023 days.

This patent is subject to a terminal disclaimer.

(21) Appl. No.: 17/279,918

(22) PCT Filed: Sep. 27, 2019

(86) PCT No.: PCT/US2019/053506
§ 371 (c)(1),
(2) Date: Mar. 25, 2021

(87) PCT Pub. No.: WO2020/069347
PCT Pub. Date: Apr. 2, 2020

(65) Prior Publication Data
US 2021/0340042 A1 Nov. 4, 2021

Related U.S. Application Data

(60) Provisional application No. 62/855,208, filed on May 31, 2019, provisional application No. 62/792,971, filed on Jan. 16, 2019, provisional application No. 62/737,322, filed on Sep. 27, 2018, provisional application No. 62/737,255, filed on Sep. 27, 2018.

(51) Int. Cl.
| | |
|---|---|
| *C12N 1/20* | (2006.01) |
| *B09C 1/10* | (2006.01) |
| *C02F 3/34* | (2023.01) |
| *C02F 11/02* | (2006.01) |
| *C02F 101/36* | (2006.01) |

(52) U.S. Cl.
CPC ............... *C02F 3/342* (2013.01); *B09C 1/10* (2013.01); *C02F 11/02* (2013.01); *C02F 2101/36* (2013.01); *C12N 1/20* (2013.01)

(58) Field of Classification Search
CPC ....................................................... C12N 1/20
See application file for complete search history.

(56) References Cited

U.S. PATENT DOCUMENTS 11,807,563 B2 * 11/2023 Jaffe .................. B09C 1/002
2015/0321933 A1 11/2015 Jaffe et al.

OTHER PUBLICATIONS

U.S. Appl. No. 18/533,781, filed 2023.*
International Search Report and Written Opinion corresponding to PCT/US2019/053506, mailed Feb. 6, 2020, 18 pages.
Liou et al., Investigating the biodegradability of perfluorooctanoic acid, Chemosphere, vol. 80, Apr. 3, 2010 [retrieved on Jan. 10, 2020). Retrieved from the Internet: <URL:https://www.sciencedirect.com/science/article/pii/0045653510002924>, pp. 176-183.
Dinglasan et al., Fluorotelomer Alcohol Biodegradation Yields Poly- and Perfluorinated Acids, Environmental Science & Technology , vol. 38, No. 10, Apr. 16, 2004 [retrieved on Jan. 11, 2020]. Retrieved from the Internet: <URL: https://pubs.acs.org/doi/abs/10.1021/es0350177>, pp. 2857-2864.
Kochunarayanan, Biodegradation Potential of Perfluorooctanoate and Perfluorooctane Sulfonate, Thesis Submitted to the Office of Graduate Studies of Texas A&M University, Aug. 2011 [retrieved on Jan. 9, 2020). Retrieved from the Internet: <URL:http://oaktrust.library.tamu.edu/bitstream/handle/1969.1/ETD-TAMU-2011-08-10177/THELAKKAT-KOCHUNARAYANAN-THESIS.pdf?sequence=2&isAllowed=y>, pp. 1-37.
Ruiz-Uriguen et al., Feammox Acidimicrobiaceae bacterium A6, a lithoautotrophic electrode-colonizing bacterium, Authors Manuscript, Apr. 14, 2018 [retrieved on Jan. 9, 2020]. Retrieved from the Internet: <URL:https://www.biorxiv.org/content/10.1101/300731v1.full.pdf>. pp. 1-30.
Ochoa-Herrera et al., Reductive Defluorination of Perfluorooctane Sulfonate, Environmental Science & Technology, vol. 42, No. 9, Mar. 28, 2008, pp. 3260-3264.
Huang et al., Defluorination of Perfluorooctanic Acid (PFOA) and Perfluorooctane Sulfonate (PFOS) by *Acidimicrobium* sp. Strain A6, Environmental Science & Technology, vol. 53, Sep. 18, 2019, pp. 11410-11419.

* cited by examiner

*Primary Examiner* — Ruth A Davis
(74) *Attorney, Agent, or Firm* — J. Clinton Wimbish; Maynard Nexsen PC

(57) ABSTRACT

Media are described herein for the degradation and/or remediation of fluorochemicals. Briefly, a medium comprises an electron donor; a fluorochemical component; an electron acceptor; and a Feammox bacterium and/or one or more enzymes exhibiting reductive dehalogenase activity, the Feammox bacterium and/or enzyme(s) capable of fluorochemical degradation in conjunction with oxidation of electron donor and electron transfer to the electron acceptor. In some embodiments, the fluorochemical component comprises one or more fluorochemicals selected from the group consisting of perfluoroalkyl compounds, polyfluoroalkyl compounds, fluorinated carboxylic acids, fluorinated alcohols, and fluorinated sulfonates. The medium, in some embodiments, comprises water, soil, sludge, sorbents and/or solids contaminated with the fluorochemical component.

26 Claims, 9 Drawing Sheets
Specification includes a Sequence Listing.

BIODEGRADATION OF FLUOROCHEMICALS

RELATED APPLICATION DATA

This application is a U.S. National Phase of PCT/US2019/053506, filed Sep. 27, 2019, which claims priority pursuant to 35 U.S.C. § 119(e) to U.S. Provisional Application Ser. Nos. 62/737,255 and 62/737,322 filed Sep. 27, 2018, U.S. Provisional Patent Application Ser. No. 62/792,971 filed Jan. 16, 2019, and U.S. Provisional Patent Application Ser. No. 62/855,208 filed May 31, 2019, each of which is incorporated herein by reference in its entirety.

FIELD

The present invention relates to systems and methods for the degradation of fluorochemicals and, in particular, to systems and methods employing microorganisms for fluorochemical degradation. The Sequence Listing titled "Sequence Listing," having a file size of 2,867,945 bytes, created on Sep. 29, 2017 and filed herewith is incorporated herein by reference as if fully set forth.

BACKGROUND

Per- and polyfluoroalkyl substances (PFAS) are emerging contaminants present in many consumer goods. These fluorochemicals are of significant concern due to their potential health effects. Because of their high water solubility, they are ubiquitous in drinking water sources, including groundwater, which becomes the main source of exposure to humans. Efforts in sustainable manufacturing of chemical compounds require that compounds for release into the environment are degradable. PFAS are very stable and little is known about their biodegradability. Even less is known about their mineralization (complete biodegradation to $CO_2$, $F^-$, and water, etc).

Release of polyfluoroalkyl chemicals into the environment can result in the formation of perfluoroalkyl carboxylic (PFCAs) and sulfonic acids (PFSAs), such as perfluorooctanoic acid (PFOA) and perfluorooctane sulfonic acid (PFOS). These compounds are highly persistent and detected widely in the environment. It is unclear if these smaller moieties can be mineralized and, so far, a lack of mineralization data has been reported. Moreover, multiple studies on the degradation of various PFAS concluded that these compounds are stable in the environment.

SUMMARY

In view these problems, media are described herein for the degradation and/or remediation of fluorochemicals. Briefly, a medium comprises an ammonium component, a fluorochemical component, an electron acceptor, and a Feammox bacterium and/or enzyme(s) thereof capable of fluorochemical degradation in conjunction with oxidation of ammonium and electron transfer to the electron acceptor.

In another aspect, a medium comprises an electron donor, a fluorochemical component, an electron acceptor, and a Feammox bacterium and/or one or more enzymes exhibiting reductive dehalogenase activity, the Feammox bacterium and/or enzyme(s) capable of fluorochemical degradation in conjunction with oxidation of electron donor and electron transfer to the electron acceptor. In some embodiments, the electron donor is molecular hydrogen ($H_2$). In some embodiments where the electron donor comprises hydrogen, fluorochemical degradation may proceed in the absence of ammonium. As detailed further herein, the electron acceptor can be fluorine and/or the fluorochemical component, resulting in the production of fluoride. Fluorine electron acceptor can be derived from the fluorochemical component, in some embodiments. The fluorochemical component, in some embodiments, comprises one or more fluorochemicals selected from the group consisting of perfluoroalkyl compounds, polyfluoroalkyl compounds, fluorinated carboxylic acids, fluorinated alcohols, and fluorinated sulfonates. The medium, in some embodiments, comprises water, soil, sludge, sorbents, and/or any solid contaminated with one or more fluorochemicals.

In another aspect, systems for environmental remediation are provided. In some embodiments, a system comprises a reactor, the reactor comprising a medium including an ammonium component, a fluorochemical component, an electron acceptor, and a Feammox bacterium and/or enzyme(s) thereof capable of fluorochemical degradation in conjunction with oxidation of ammonium and electron transfer to the electron acceptor. Alternatively, the medium in the reactor comprises an electron donor, a fluorochemical component, an electron acceptor, and a Feammox bacterium and/or enzyme(s) exhibiting reductive dehalogenase activity, the Feammox bacterium and/or enzyme(s) capable of fluorochemical degradation in conjunction with oxidation of the electron donor and electron transfer to the electron acceptor. In some embodiments, the electron donor is molecular hydrogen ($H_2$). The reactor can comprise an inlet and outlet for the medium, such as a water and/or soil. The reactor, for example, can be operated continuously or in a batch mode.

In another aspect, methods of environmental remediation are described herein. A method, in some embodiments, comprises providing a medium comprising an ammonium component, a fluorochemical component, and an electron acceptor. A Feammox bacterium and/or enzyme(s) thereof are disposed in the medium. The fluorochemical component is degraded by the Feammox bacterium and/or enzyme(s) thereof in conjunction with oxidation of ammonium and electron transfer to the electron acceptor. Alternatively, the ammonium component may be partially or fully replaced by molecular hydrogen ($H_2$), and the fluorochemical component is degraded by the Feammox bacterium and/or enzyme(s) thereof in conjunction with oxidation of the hydrogen and electron transfer to the electron acceptor.

In other embodiments, a method of environmental remediation comprises providing a medium comprising an electron donor and a fluorochemical component. A Feammox bacterium and/or one or more enzymes exhibiting reductive dehalogenase activity are disposed in the medium. The fluorochemical component is degraded by the Feammox bacterium and/or one or more enzymes in conjunction with oxidation of electron donor and electron transfer to an electron acceptor. In some embodiments, the electron donor is molecular hydrogen ($H_2$). The electron acceptor, in some embodiments, is fluorine resulting the production of fluoride. The fluorine can be derived from decomposition of the fluorochemical component, in some embodiments.

In some embodiments, the fluorochemical component comprises one or more fluorochemicals selected from the group consisting of perfluoroalkyl compounds, polyfluoroalkyl compounds, fluorinated carboxylic acids, fluorinated alcohols, and fluorinated sulfonates, including fluorotelomer sulfonate and fluorotelomer alcohol. The medium, in some embodiments, comprises water, soil, sludge, sorbents, and/or any solid contaminated with one or more fluorochemicals.

DETAILED DESCRIPTION

Figures 1A, 1B:
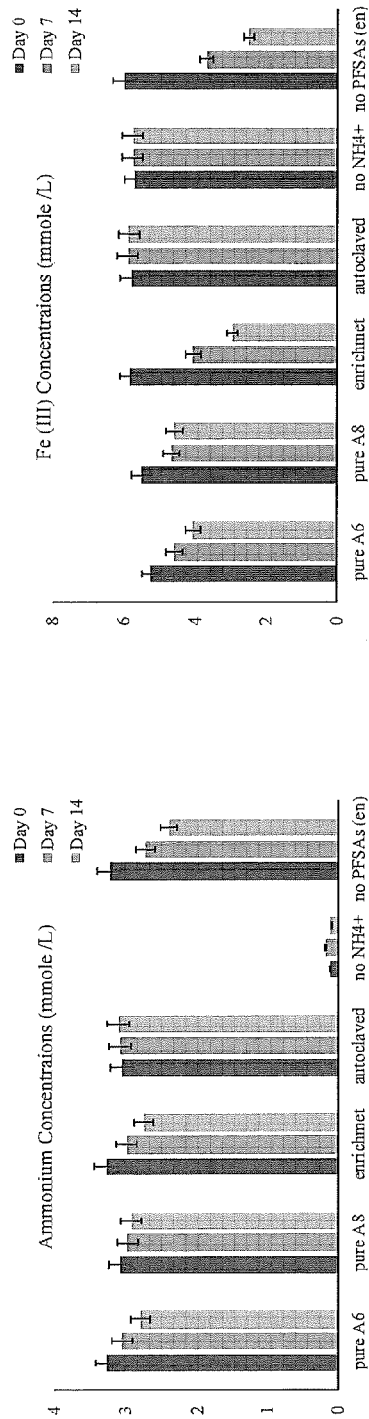
FIGS. 1(a)-(d) illustrate the results from Heptafluorobutyric Acid (HFBA) incubations according to some embodiments.

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

"Synthetic nucleic acid sequence," "synthetic polynucleotide," "synthetic oligonucleotide," "synthetic DNA," or "synthetic RNA" as used herein refers to a nucleic acid, polynucleotide, oligonucleotide, DNA, or RNA that differs from one found in nature by having a different sequence than one found in nature or a chemical modification not found in nature. The definition of synthetic nucleic acid includes but is not limited to a DNA sequence created using biotechnology tools. Such tools include but are not limited to recombinant DNA technology, chemical synthesis, or directed use of nucleases (so called "genome editing" or "gene optimizing" technologies).

Embodiments described herein can be understood more readily by reference to the following detailed description and examples and their previous and following descriptions. Elements and apparatus described herein, however, are not limited to the specific embodiments presented in the detailed description. It should be recognized that these embodiments are merely illustrative of the principles of the present invention. Numerous modifications and adaptations will be readily apparent to those of skill in the art without departing from the spirit and scope of the invention.

In one aspect, media are described herein for the degradation and/or remediation of fluorochemicals. A medium, for example, comprises an ammonium component, a fluorochemical component, an electron acceptor, and a Feammox bacterium and/or enzyme(s) thereof capable of fluorochemical degradation in conjunction with oxidation of ammonium and electron transfer to the electron acceptor. In another aspect, a medium comprises an electron donor, a fluorochemical component, an electron acceptor, and a Feammox bacterium and/or enzyme(s) exhibiting reductive dehalogenase activity capable of fluorochemical degradation in conjunction with oxidation of the electron donor and electron transfer to the electron acceptor. As detailed further herein, the electron donor can be molecular hydrogen ($H_2$), in some embodiments. Moreover, the electron acceptor can be fluorine and/or the fluorochemical component resulting in the production of fluoride, in some embodiments. Fluorine electron acceptor can be derived from the fluorochemical component, in some embodiments. The medium, in some embodiments, comprises water, soil, sludge, sorbents and/or any solid contaminated with one or more fluorochemicals.

Turning now to specific components, the medium, in some embodiments, comprises an ammonium component. The ammonium component can comprise ammonium and/or compound(s) comprising ammonium. Ammonium containing compounds, for example, can comprise fertilizers, domestic sewage, or industrial effluents. The ammonium component may comprise ammonium chloride and/or any other ammonium salt. The ammonium component may also be a nitrogen containing organic compound, wherein nitrogen may be hydrolyzed to ammonium.

In other embodiments, the medium comprises an electron donor. Any electron donor operable to undergo oxidation with electron transfer to the electron acceptor can be used. An electron donor, in some embodiments, can be an ammonium component described above. Alternatively, an electron donor can be molecular hydrogen ($H_2$) or an organic compound, including various carbon-containing compounds. An organic compound, for example, can be oxidized to $CO_2$ with electron transfer to the electron acceptor. The organic compound(s) can also be fermented, producing hydrogen ($H_2$), which is then used as the electron donor. Specific identity of the electron donor can be dependent on several considerations including identity of the reductive dehalogenase(s).

The fluorochemical component of the medium can comprise one or more fluorinated organic compounds. In some embodiments, the fluorochemical component comprises one or more fluorochemicals selected from the group consisting of perfluoroalkyl compounds, polyfluoroalkyl compounds, fluorinated carboxylic acids, fluorinated alcohols, and fluorinated sulfonates. In some embodiments, the fluorochemical component comprises one or more compounds selected from Table I.

TABLE I

| Fluorochemicals |
|---|
| Heptafluorobutyric acid (HFBA) |
| Perfluorooctanoic acid (PFOA) |
| 2,2,2-Trifluoroethyl Nonafluorobutanesulfonate (PFBS) |
| 6:2 Fluorotelomer sulfonate (6:2 FTS) |
| 8:2 Fluorotelomer Alcohol (8:2 FTOH) |
| Ammonium 4,8-dioxa-3H-perfluorononanoate (ADONA) |
| Perfluorobutanoic acid (PFBA) |
| Perfluorooctane sulfonamide (FOSA) |
| Perfluorooctane sulfonate (PFOS) |
| Perfluoroheptane sulfonate (PFHpS) |
| Perfluorohexane sulfonate (PFHxS) |
| Perfluoropentanoic acid (PFHeA) |
| Perfluoroheptanoic acid (PFHpA) |
| Perfluorohexanoic acid (PFHxA) |
| Perfluoropentane sulfonate (PFPeS) |
| Pentafluoropropionic acid (PFPrA) |

TABLE I-continued

Fluorochemicals

6:2 Fluorotelomer alcohol (6:2 FTOH)
8:2 Fluorotelomer phosphate diester (8:2 diPAP)
8:2 Fluorotelomer sulfonate (8:2 FTS)

The medium also comprises an electron acceptor. In some embodiments, the electron acceptor is a transition metal. Transition metal acceptors, in some embodiments, comprise metal oxyhydroxides. For example, the electron acceptor can be Fe(III). In some embodiments, the electron acceptor comprises iron oxide, a goethite, elemental iron, a nontronite, iron-rich clay or various mixtures thereof. Iron oxide can include hydrated forms, such as ferrihydrite. Ferrihydrite includes a dark brown or yellow brown mineral composed of about 20% ($FeO_4$) and 80% ($FeO_6$) polyhedral. The term "goethite" refers to an iron oxyhydroxide containing ferric iron. The term "nontronite" refers to the Fe(III) rich clay mineral having a typical structural formula $Ca_{0.5}(Si_7Al_{0.8}Fe_{0.2})(Fe_{3.5}Al_{0.4}Mg_{0.1})O_{20}(OH)_4$. The Fe(III) source may be scrap metal, or any other source of ferric iron.

In some embodiments, Fe(III) is present in the medium at a concentration of 1 mM to 200 mM. The concentration of Fe(III) may also be from 1 mM to 2 mM, from 2 mM to 3 mM, from 3 mM to 4 mM, from 4 mM to 5 mM, from 5 mM to 6 mM, from 6 mM to 7 mM, from 7 mM to 8 mM, from 8 mM to 9 mM, from 9 mM to 10 mM, from 10 mM to 20 mM, from 20 mM to 30 mM, from 30 mM to 40 mM, from 40 mM to 50 mM, from 50 mM to 60 mM, from 60 mM to 70 mM, from 70 mM to 80 mM, from 80 mM to 90 mM, from 90 mM to 100 mM, from 100 mM to 150 mM, or from 150 mM to 200 mM.

Alternatively, the electron acceptor can be an anode. In such embodiments, the medium may be part of a bioelectrochemical reactor, such as a microbial electrolysis cell (MEC). The anode can replace chemical species, such as iron, that undergo reduction in the Feammox process. In this way, the medium is not limited by the required presence of a metal acceptor. The presence of an anode, for example, can permit degradation of fluorochemicals in the absence of iron and/or other metal species. In some embodiments, the Feammox bacterium colonizes the anode.

In some embodiments, the electron acceptor is fluorine and/or the fluorochemical component resulting the in the production of fluoride. Fluorine electron acceptor in the medium, in some embodiments, can be derived from the fluorochemical component. Degradation of the fluorochemical component by the Feammox bacterium and/or one or more enzymes exhibiting reductive dehalogenase activity in the medium, for example, can free fluorine to serve as an electron acceptor. Additionally, the electron acceptor, in some embodiments can comprise anthraquinone and/or derivatives thereof. In some embodiments, for example, the electron acceptor can comprise 9,10-anthraquinone-2,7-disulphonic acid (AQDS).

Moreover, the electron acceptor in the medium can comprise several species, in some embodiments. Electron acceptor of the medium can comprise at least two species selected from the group consisting of fluorine (and/or fluorochemical component), a transition metal, anthraquinone derivative and an electrode. In some embodiments, for example, the electron acceptor comprises fluorine and Fe(III). Additionally, in some embodiments, the electron acceptor can be limited to a single species depending on reaction conditions. In some embodiments, the electron acceptor can be limited to any one of the electron acceptors described herein. For example, in some embodiments, the electron acceptor can be limited to fluorine and/or fluorochemical component, especially in embodiments where molecular hydrogen is the electron donor. In such embodiments, Fe(III) or other metal electron acceptor may be obviated, thereby expanding methods and systems described herein to environments deficient in iron.

The medium also comprises a Feammox bacterium and/or enzyme(s) thereof capable of fluorochemical degradation in conjunction with oxidation of ammonium and electron transfer to the electron acceptor. The Feammox bacterium may be an Actinobacterium or a bacterium with a similar genetic composition. In some embodiments, for example, the Feammox bacterium is an Acidimicrobiaceae bacterium or variant thereof. The Feammox bacterium may be a bacterial strain that was isolated from wetland soils collected in New Jersey after a series of enrichment incubations. The soil samples were collected at the location identified as 40°15' N-74°30' W or within 100 m of the identified location. The Feammox bacterium may be the bacterial strain designated the Acidimicrobiaceae Feammox bacterium A6 or variant thereof. In being a variant in some embodiments, the bacterium may have at least 70% genome overlap with an Actinobacterium. The Acidimicrobiaceae Feammox bacterium A6 was submitted for deposit with the American Type Culture Collection (ATCC; 10801 University Blvd. Manassas, Virginia 20110-2209, USA) on Apr. 27, 2015, the submission was supplemented on May 7, 2015, and was assigned Accession Deposit Number PTA-122488 on Sep. 17, 2015. The Acidimicrobiaceae Feammox bacterium may have a genome comprising, consisting essentially of, or consisting of a nucleic acid sequence with at least 70, 72, 75, 80, 85, 90, 91, 92, 93, 94, 95, 96, 97, 98, 99, or 100% identity to SEQ ID NO: 1. The Feammox bacterium may have the genome size of 3.3 mega base pairs (Mb) and guanine-cytosine content 52%. The bacterial genome may further include a gene encoding a Feammox Ammonium Monooxygenase. As used herein, the term "Feammox Ammonium Monooxygenase" (FMO) refers to an enzyme that plays a key role in oxidizing ammonium coupled with ferric iron reduction. The FMO also refers to genes encoding clones or different variants of the Feammox Ammonium Monooxygenase. The gene may include a nucleic acid comprising, consisting essentially of, or consisting of a nucleic acid sequence with at least 70, 72, 75, 80, 85, 90, 91, 92, 93, 94, 95, 96, 97, 98, 99, or 100% identity to a sequence selected from the group consisting of: SEQ ID NOS: 8-28. The Feammox Ammonium Monooxygenase may include an amino acid comprising, consisting essentially of, or consisting of a nucleic acid sequence with at least 70, 72, 75, 80, 85, 90, 91, 92, 93, 94, 95, 96, 97, 98, 99, or 100% identity to a sequence selected from the group consisting of: SEQ ID NOS: 29-49. The Feammox bacterium may be live or lyophilized.

| SEQ ID NOS of FMO Related Enzymes and Genes | | |
|---|---|---|
| FMO clone* | SEQ ID NO (Gene) | SEQ ID NO (Enzyme) |
| ERCFMO_0001 | 8 | 29 |
| ERCFMO_0002 | 9 | 30 |
| ERCFMO_0003 | 10 | 31 |
| ERCFMO_0004 | 11 | 32 |
| ERCFMO_0005 | 12 | 33 |
| ERCFMO_0006 | 13 | 34 |
| ERCFMO_0007 | 14 | 35 |

-continued

| SEQ ID NOS of FMO Related Enzymes and Genes | | |
|---|---|---|
| FMO clone* | SEQ ID NO (Gene) | SEQ ID NO (Enzyme) |
| ERCFMO_0008 | 15 | 36 |
| ERCFMO_0009 | 16 | 37 |
| ERCFMO_0010 | 17 | 38 |
| ERCFMO_0011 | 18 | 39 |
| ERCFMO_0012 | 19 | 40 |
| ERCFMO_0013 | 20 | 41 |
| ERCFMO_0014 | 21 | 42 |
| ERCFMO_0015 | 22 | 43 |
| ERCFMO_0016 | 23 | 44 |
| ERCFMO_0017 | 24 | 45 |
| ERCFMO_0018 | 25 | 46 |
| ERCFMO_0019 | 26 | 47 |
| ERCFMO_0020 | 27 | 48 |
| ERCFMO_0021 | 28 | 49 |

In some embodiments, Feammox bacteria and related enzymes are described in U.S. Pat. No. 9,815,723 which is incorporated herein by reference in its entirety.

Determining percent identity of two nucleic acid sequences may include aligning and comparing the nucleotides at corresponding positions in the two sequences. If all positions in two sequences are occupied by identical nucleotides then the sequences are said to be 100% identical. Percent identity may be measured by the Smith Waterman algorithm (Smith T F, Waterman M S 1981 "Identification of Common Molecular Subsequences," *J Mol Biol* 147: 195-197, which is incorporated herein by reference as if fully set forth).

Additionally, Feammox bacteria and/or related enzymes described herein may undergo alterations or modifications during the fluorochemical degradation process. Alterations or modifications to the Feammox bacteria and/or related enzymes can be dependent on reactions conditions, in some embodiments. For example, in the presence of molecular hydrogen as the electron donor, the Feammox bacteria can lose its plasmid and the concomitant ability to oxidize ammonium. As the plasmid is distinct from chromosomal DNA, the loss of the plasmid does not render the Feammox bacteria a different organism falling outside the claims and scope of the present disclosure. Notably, methods and systems described herein contemplate alterations and/or modifications to Feammox bacteria and/or related enzymes resulting from the reaction conditions and/or the degradation of fluorochemicals.

Moreover, growing Acidimicrobiaceae Feammox bacterium A6, which is an iron reducer, requires removing electron acceptors (i.e., $O_2$, $NO_3^-$) that are typically used by other organisms at higher redox potentials. During the incubation experiments described here $O_2$ was removed by flushing vials with either $N_2$ gas or a $N_2/CO_2$ mixture. The mixture of $N_2/CO_2$ is used because A6 requires $CO_2$ as its carbon source. In more complex systems where flushing with a gas is difficult, electron acceptors that are used under more oxidative conditions than Fe(III) like $O_2$ and $NO_3^-$ can also be removed by adding a carbon source to the system (i.e. reactor, groundwater, soil) so that when heterotrophic bacteria degrade the carbon source they consume the electron acceptors that are used at higher redox potentials than Fe(III) reduction. Hence, although A6 does not require organic carbon as an electron donor, some media to grow A6 may contain a biodegradable organic substrate with the goal of consuming electron acceptors such as $O_2$ or $NO_3^-$ and achieving iron reducing conditions. Removal of these electron acceptors can also be achieved via chemical means.

As described herein, the medium may comprise one or more enzymes, such as FMO, in addition to the Feammox bacterium for the degradation of fluorochemical(s) in conjunction with oxidation of the electron donor and electron transfer to the electron acceptor. Alternatively, one or more enzymes, such as FMO, can be present in the medium in the absence of the Feammox bacterium. In such embodiments, the one or more enzymes can be responsible for fluorochemical degradation. In some embodiments, for example, FMO is isolated from Feammox bacterium and employed in the media. In other embodiments, the one or more enzymes may be fabricated via synthetic chemical techniques.

In some embodiments, the medium comprises one or more enzymes exhibiting reductive dehalogenase activity for fluorochemical degradation including, but not limited to, one or more reductive dehalogenases and/or reductive dehalogenase variants. Dehalogenase content of the medium can be expressed by one or more bacterium in the medium including, but not limited to, Feammox bacteria. In some embodiments, one or more dehalogenases and/or enzymes exhibiting dehalogenase activity are present in the medium in the absence of bacteria or other expressing species. A dehalogenase, in some embodiments, described herein can have an amino acid sequence comprising at least 60% or at least 70% identity of a sequence selected from SEQ ID NOS: 50-53. In some embodiments, a dehalogenase has an amino acid sequence of 80-100% identity of a sequence selected from SEQ ID NOS: 50-53. Additionally, reductive dehalogenases described herein include genes encoding clones or different variants of the dehalogenases, including enzymes exhibiting dehalogenase activity. One or more genes, for example, can include a nucleic acid sequence comprising at least 60% or at least 70% identity of a sequence selected from SEQ ID NOS: 54-57. In some embodiments, a gene encoding a dehalogenase can include a sequence comprising 60-100% identity of a sequence selected from SEQ ID NOS: 54-57. Reductive dehalogenases falling under one or more SEQ ID NOS: 54-57 have been deposited with the International Nucleotide Sequence Database Collaboration DDBJ/EMBL/GenBank and assigned accession numbers MK358459 through MK358462.

In some embodiments, the medium further comprises one or more electron shuttling compounds. Any electron shuttling compound consistent with the objectives of fluorochemical degradation can be used. In some embodiments, an electron shuttling compound is 9,10-Anthraquinone-2,7-disulphonic acid (AQDS).

The medium can comprise water, soil, sludge, sorbents and/or any solids contaminated with fluorochemicals. The water can be any source of water, including ground water, lakes, streams and/or reservoirs. In some embodiments, the water is wastewater. As used herein, the term "wastewater" refers to any water that has been adversely affected in quality by anthropogenic influence. Wastewater may be municipal wastewater, industrial wastewater, agricultural wastewater, surface runoff, stormwater, or wastewater combining wastewater from multiple sources. Wastewater may be treated in a wastewater treatment plant. Similarly, soil may be any soil that has been adversely affected in quality by anthropogenic influence. The soil may include groundwater. The groundwater may comprise wastewater described herein.

In some embodiments, the medium may further comprise a carrier. The carrier may support growth of the Feammox bacterium. The carrier may comprise a filter, beads, agarized medium, or any surface that allows bacterial attachment. The carrier may include media for culturing the Feammox bacterium. The media may be inorganic $NH_4^+$-ferric iron media. The inorganic $NH_4^+$-ferric iron media may be solid media or liquid media. The liquid media may include but not limited to the following components: $NH_4Cl$, $(NH_4)_2SO_4$, $NaHCO_3$, $KHCO_3$, $KH_2PO4$, 100 mg $MgSO_4.7H_2O$, and $CaCl_2.2H_2O$. The liquid media may further include ferrihydrite, AQDS, trace element solution or vitamins. Vitamins may be but are not limited to ATCC® vitamins The liquid media may have a pH in a range from 2.0 to 8.0. The media may include traces of dissolved oxygen. The solid medium may have the same composition as the liquid media but include elements to solidify the mixture. The solid media may be solidified with 0.8% agar. The solid media may include ferrihydrite that is spread on the surface of the medium.

In another aspect, systems for environmental remediation are provided. In some embodiments, a system comprises a reactor, the reactor comprising a medium including an ammonium component, a fluorochemical component, an electron acceptor, and a Feammox bacterium and/or enzyme(s) thereof capable of fluorochemical degradation in conjunction with oxidation of ammonium and electron transfer to the electron acceptor. Alternatively, the medium in the reactor comprises an electron donor, a fluorochemical component, an electron acceptor, and a Feammox bacterium and/or enzyme(s) exhibiting reductive dehalogenase activity capable of fluorochemical degradation in conjunction with oxidation of the electron donor and electron transfer to the electron acceptor. In some embodiments, the electron donor is molecular hydrogen ($H_2$). As detailed further in the examples, molecular hydrogen may replace the ammonium component in the fluorochemical degradation process.

In some embodiments, the reactor comprises an inlet and outlet for the medium, such as a water and/or soil. The reactor, for example, can be operated continuously or in a batch mode. Components of the medium, including the ammonium component or electron donor, fluorochemical component, electron acceptor and Feammox bacterium and/or enzyme(s) thereof can have any properties and/or compositions described hereinabove. Moreover, the medium can comprise water, soil, sludge, sorbents, and/or any solid contaminated with one or more fluorochemicals. Water of the system can be any source of water, including wastewater, ground water, lakes, streams and/or reservoirs.

The reactor may be a continuous reactor or a batch reactor. In an embodiment, a reactor may be an industrial-type reactor. The reactor may operate within a water treatment plant. The reactor may be a treatment pond or a reservoir. The reactor may be a tank for wastewater storage.

Reactor conditions may generally include a temperature in a range from 4° C. to 35° C. The temperature may be in a range between any two integer value temperatures selected from 4° C. to 35° C. The temperature may be in a range between and including 4° C. to 10° C., 10° C. to 15° C., 15° C. to 20° C., 20° C. and 25° C., 25° C. and 30° C., 30° C. and 35° C. The temperature may be any one integer value temperature selected from those including and between 4° C. and 35° C. or 15° C. to 35° C. Temperatures between room temperature and 35° C. may be used. The temperature may be any one temperature including and between room temperature and 35° C. Temperatures between 20° C. and 35° C. may be used. The temperature may be any temperature including and between 20° C. and 25° C.

The reactor may be operated for any desired time period. In some embodiments, the reactor is operated for a time period ranging from 2 hours to 45 days. The time period may be 5 hours, 10 hours, 15 hours, 20 hours, 1 day, 2 days, 3 days, 4 days, 5 days, 10 days, 15 days, 20 days, 25 days, 30 days, 35 days, 40 days or 45 days. The time period may be any one integer value selected from those including and between value points, endpoints inclusive. The time period may be greater than 45 days. The time period may be less than 1 day. In continuous flow reactors or in batches, the process may last from several hours to several months. For continuous flow reactors, the time period may depend on the bacterial concentration in the inoculum. Higher bacterial concentration in the inoculum may result in a shorter remediation time. The time period may depend on hydraulic retention capacity of a continuous flow reactor. Lower retention capacity of the continuous flow reactor may result in a shorter remediation time. Hydraulic residence time for the continuous flow reactors may be from 3 hours to 4 hours, from 3 hours to 5 hours, from 3 hours to 6 hours, from 3 hours to 7 hours, from 3 hours to 8 hours, from 3 hours to 10 hours, from 3 hours to 15 hours, from 3 hours to 20 hours, from 3 hours to 1 day, from 3 hours to 2 days, from 3 hours to 3 days or longer. Hydraulic residence time may be any integer value selected from those including and between value points, endpoints inclusive.

pH of the medium in the reaction can range from 2.0 to 8.0. The pH of the medium may be in a range between and including 2.0 and 3.0, 3.0 and 4.0, 4.0 and 5.0, 5.0 and 6.0, 6.0 to 7.0, 7.0 to 7.5. The pH may be any one integer value pH selected from those including and between 2.0 and 7.5. The pH may be any pH including and between 4.0 and 7.0.

In another aspect, methods of environmental remediation are described herein. A method, in some embodiments, comprises providing a medium comprising an ammonium component, a fluorochemical component, and an electron acceptor. A Feammox bacterium and/or enzyme(s) are thereof are disposed in the medium. The fluorochemical component is degraded by the Feammox bacterium and/or enzyme(s) thereof in conjunction with oxidation of ammonium and electron transfer to the electron acceptor. In some embodiments, the ammonium component may be partially or fully replaced by molecular hydrogen ($H_2$) in the degradation of the fluorochemical component.

In other embodiments, a method of environmental remediation comprises providing a medium comprising an electron donor and a fluorochemical component. A Feammox bacterium and/or one or more enzymes exhibiting reductive dehalogenase activity are disposed in the medium. The fluorochemical component is degraded by the Feammox bacterium and/or one or more enzymes in conjunction with oxidation of the electron donor and electron transfer to an electron acceptor. The electron donor, in some embodiments, is molecular hydrogen ($H_2$). The electron acceptor, in some embodiments, is fluorine and/or the fluorochemical component resulting the production of fluoride. The fluorine can be derived from decomposition of the fluorochemical component, in some embodiments.

In some embodiments, the fluorochemical component comprises one or more fluorochemicals selected from the group consisting of perfluoroalkyl compounds, polyfluoroalkyl compounds, fluorinated carboxylic acids, fluorinated alcohols, and fluorinated sulfonates, including fluorotelomer sulfonate and fluorotelomer alcohol. The fluorochemical component, for example, can be selected from Table I. The medium, in some embodiments, comprises water, soil or mixtures thereof.

Components of the medium, including the ammonium component or electron donor, fluorochemical component, electron acceptor and Feammox bacterium and/or enzyme(s) thereof can have any properties and/or compositions described hereinabove. Moreover, the medium can comprise water and/or soil. Water of the system can be any source of water, including wastewater, ground water, lakes, streams and/or reservoirs.

These and other embodiments are further illustrated by the following non-limiting examples.

Example 1—Fluorochemical Degradation

Materials and Methods

Toxicity experiments were conducted for both pure and enrichment cultures with selected PFAS Compounds. The concentrations to test were 1 ppb, 10 ppb, 100 ppb and 1 ppm. During 14 days incubation, no toxicity of Heptafluorobutyric acid (HFBA), Perfluorooctanoic acid (PFOA) was evidenced by cultures with these concentrations. However, the growing of biomass was slightly inhibited when the concentration of 2,2,2-Trifluoroethyl Nonafluorobutanesulfonate (PFBS) was 1 ppm in the pure culture incubations.

All Incubations were conducted in 20-ml serum vials with a pure strain A6 (Acidimicrobiaceae sp.)/A8 (*Terrimonas* sp.) or an enrichment culture, which contained 40.1-48.5% of Acidimicrobiaceae sp. A6, and in the anoxic inorganic Fe(III)-$NH_4^+$ enrichment medium. The composition of the inorganic Fe(III)-$NH_4^+$ enrichment medium (pH 4.5-5.0) consisted of 504 mg/L 2-line ferrihydrite [$Fe_2O_3 \cdot 0.5H_2O$], 177 mg/l $NH_4Cl$, 77.9 mg/L $(NH_4)_2SO_4$, 19.8 mg/L $NaHCO_3$, 71.0 mg/L $KHCO_3$, 9.00 mg/L $KH_2PO_4$, 100 mg/L $MgSO_4 \cdot 7H_2O$, and 60.0 mg/L $CaCl_2 \cdot 2H_2O$, in addition to 1 ml/L of a trace element solution, and 1 ml/L of a vitamin solution (ATCC® MD-VS™). An electron shuttling compound, 9,10-Anthraquinone-2,7-disulphonic acid (AQDS), was added to the pure strain A6 with a final concentration as 0.05 mg/L. To achieve strictly anoxic conditions, the headspace of each incubation vial was vacuumed until no bubble formation was observed and then flushed with a $N_2/CO_2$ (80:20) gas mixture, which was repeated 3 times. Then, for the PFAS degradation experiment, an equal volume of either HFBA, PFOA and PFBS was added to each group of vials, to yield final concentrations to 100 ppb. In the control group, autoclave control, without PFASs and without addition of $NH_4^+$ were prepared. All These vials were placed on a shaker (100 rpm) in an anaerobic glove box for 14-day incubations at ambient temperature. Duplicate samples were collected destructively every week for Fe(II), $NH_4^+$, and HFBA/PFOA/PFBS analyses.

| Cultures | PFAS (1 ppm) | PFAS (100 ppb) | PFAS (10 ppb) | PFAS (1 ppb) |
|---|---|---|---|---|
| A6 (ID: A4-a) | * | † | * | * |
| A8 (ID: H3-a) | * | † | * | * |
| Enrichment | * | † | * | * |
| No iron | | † | | |
| No ammonium | | † | | |
| Media only | | † | | |

*Toxicity experiment
† Biodegradation experiment

Results

Toxicity experiments, in terms of how each of these PFAS affects the biomass over a 14-day incubation, were conducted for both pure and enrichment cultures. The concentrations tested were 1 ppb, 10 ppb, 100 ppb and 1 ppm. During 14 days of incubation, no effects by Heptafluorobutyric acid (HFBA) and Perfluorooctanoic acid (PFOA) on the overall bacterial numbers were detected for these concentrations. However, the biomass growth was inhibited when the concentration of 2,2,2-Trifluoroethyl Nonafluorobutanesulfonate was 1 ppm in the incubation with the pure culture.

Figures 1C, 1D:
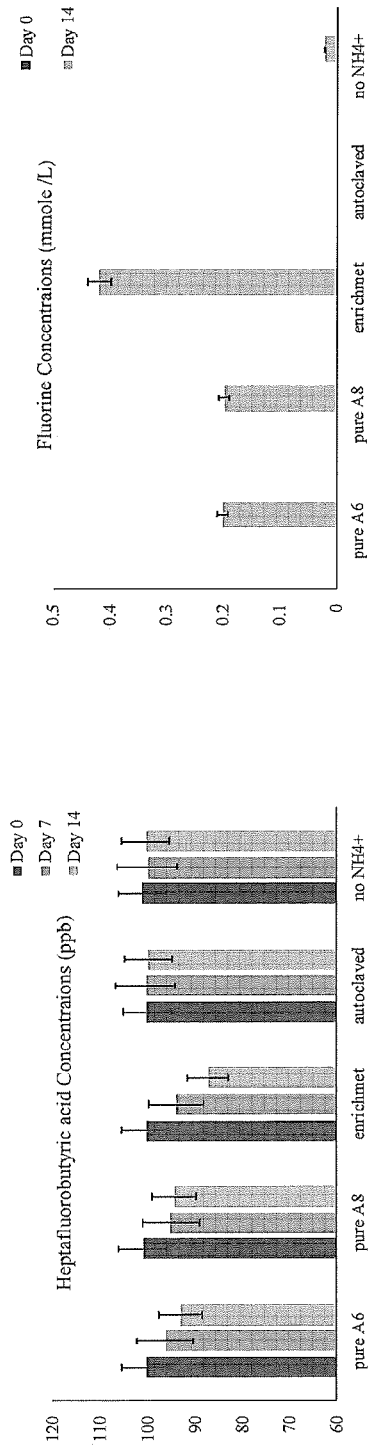
Figures 2A, 2B:
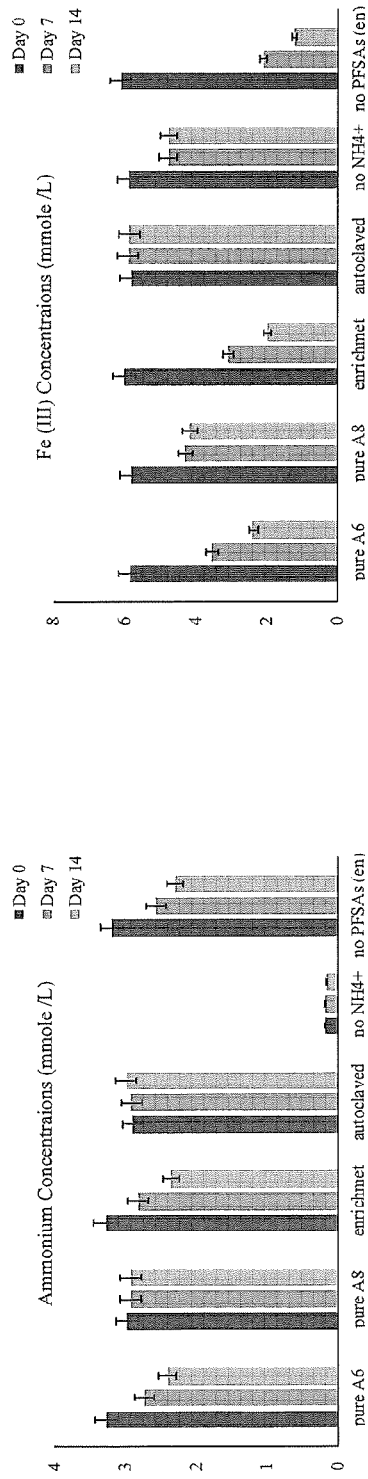
FIGS. 2(a)-(d) illustrate the results from Perfluorooctanoic Acid (PFOA) incubations according to some embodiments.
Figures 2C, 2D:
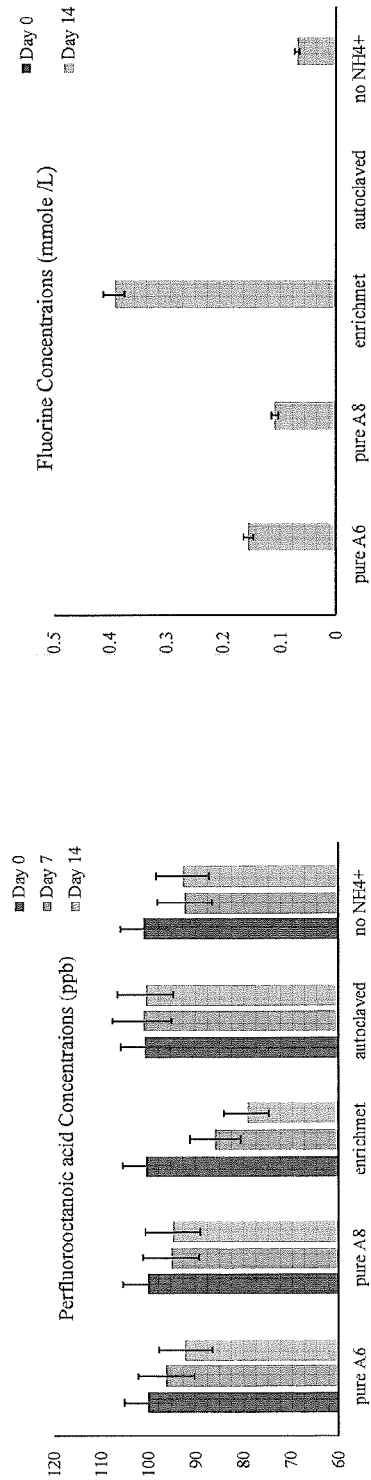
Figures 3A, 3B:
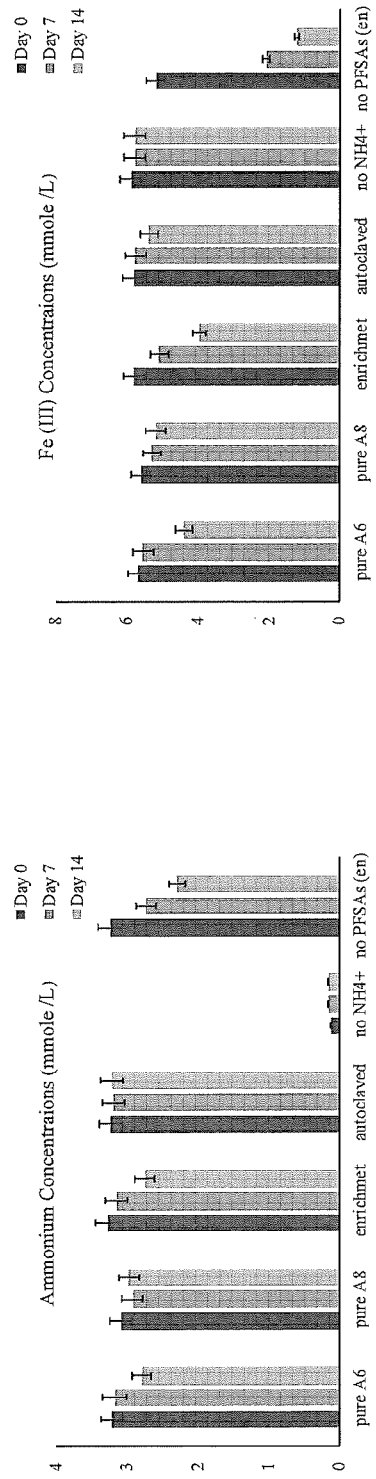
FIGS. 3(a)-(d) illustrate the results from 2,2,2-Trifluoroethyl Nonafluorobutanesulfonate (PFBS) incubations according to some embodiments.
Figures 3C, 3D:
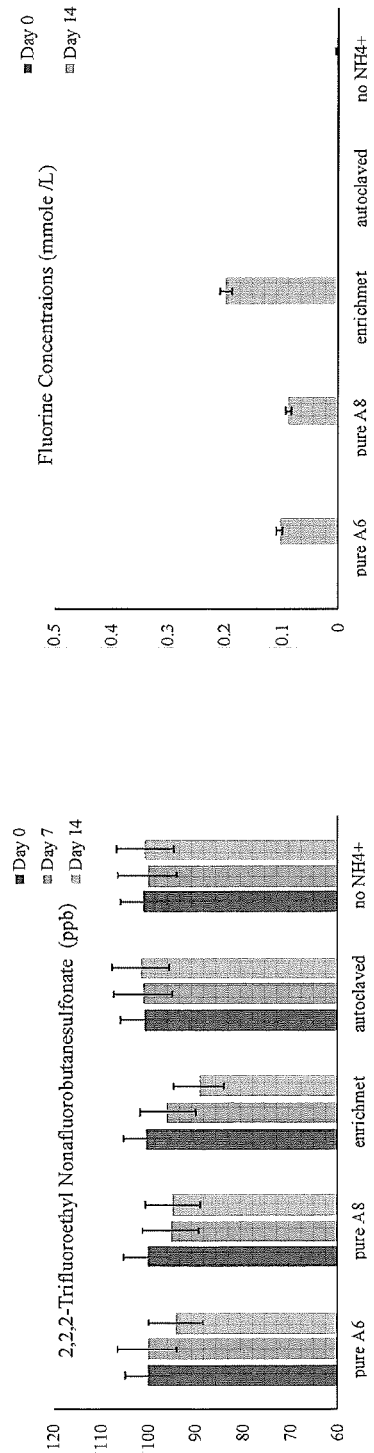

Based on these results, all incubations were conducted at an initial PFAS concentration of 100 ppb. FIGS. 1 to 3 show results of the incubations in the presence and absence of these PFAS over a 14-day period. Results are shown for each PFAS results with the pure strain of A6, a pure strain A8, a Feammox enrichment culture, an autoclaved sample, an incubation to which no $NH_4^+$ was added, and a Feammox enrichment culture without PFAS. For each of these runs data is shown for: (a) $NH_4^+$ removal, (b) Fe(II) production, (c) PFAS removal, and (d) fluoride ($F^-$) production.

First it should be noted that in all cases the Feammox activity, measured in terms of $NH_4^+$ removal and Fe(II) production, was higher in the absence of the PFAS, indicating that at 100 ppb there was still some toxicity/inhibition by these PFAS on the Feammox process.

Figure 4:
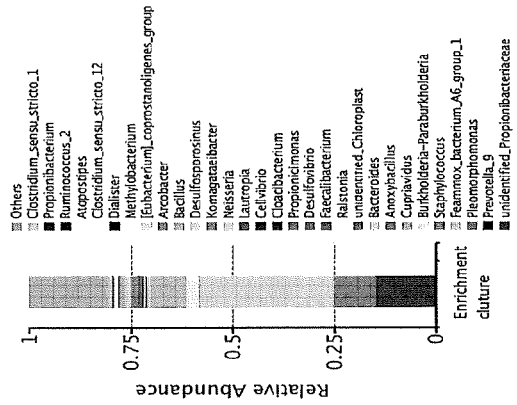
FIG. 4 illustrates the community analysis of a medium for fluorochemical degradation according to some embodiments.

Results shown in FIGS. 1 through 3 show that all 3 PFAS are being degraded and higher removal was observed in the enrichment culture, which in terms of $NH_4^+$ removal and Fe(III) reduction also had higher Feammox activity. No degradation intermediates were observed in the chromatogram of the HFBA, and PFOA, while a new peak appeared in the PFBS samples, indicating a degradation intermediate. Still, Fluoride ($F^-$) production indicates possible mineralization of these PFAS in these incubations. Results of a community analysis of the enrichment culture is shown in FIG. 4, showing that tat about 40% of the bacterial population in the enrichment culture was Acidimicrobiaceae sp. A6.

Additional fluorochemical species were tested in accordance with the parameters of this Example. The full results of fluorochemical degradation are provided in Table II.

TABLE II

Summary of Fluorochemical Degradation

Heptafluorobutyric acid (HFBA) (100 ppb)

| | pure A6 | pure A8 | enrichment | autoclaved |
|---|---|---|---|---|
| Two week removal (%) | 7.20% | 10.44% | 20.07% | 0.31% |

Perfluorooctanoic acid (PFOA) (100 ppb)

| | pure A6 | pure A8 | enrichment | autoclaved |
|---|---|---|---|---|
| Two week removal (%) | 7.92% | 5.38% | 20.98% | 0.18% |

2,2,2-Trifluoroethyl Nonafluorobutanesulfonate (PFBS) (100 ppb)

| | pure A6 | pure A8 | enrichment | autoclaved |
|---|---|---|---|---|
| Two week removal (%) | 5.92% | 5.38% | 11.02% | −0.81% |

6:2 Fluorotelomer sulfonate (6:2 FTS) (100 ppb)

| | pure A6 | pure A8 | enrichment | autoclaved |
|---|---|---|---|---|
| One week removal (%) | 3.05% | 2.77% | 5.84% | −0.40% |

8:2 Fluorotelomer Alcohol (8:2 FTOH) (100 ppb)

| | pure A6 | pure A8 | enrichment | autoclaved |
|---|---|---|---|---|
| One week removal (%) | 2.08% | 1.42% | 5.52% | 0.05% |

Example 2—Fluorochemical Degradation

Toxic inhibitions on A6's Feammox activity for a series of PFASs in Table III were tested up to concentrations of 100 mg/l and were found to be negligible within this range. Incubations were conducted with a pure A6 culture as well as an A6 enrichment culture, and for both cases with initial concentrations of 0.1 mg/l to 100 mg/l of these fluorinated compounds, and in a growth medium as described by Huang and Jaffé, 2018. Isolation and Characterization of an Ammonium-Oxidizing Iron Reducer: Acidimicrobiaceae sp. A6. PLOS ONE, Vol. 13, No. 4, e0194007, which contained ferrihydrite as the Fe(III) source.

TABLE III

Feammox incubation results for various PFAS using an A6 enrichment culture at day 60

| A. Compound with initial conc. 100 mg/l | B. Decrease in concentration (mg/l) | C. $F^-$ produced (mg/l) | D. % defluorination of initial compound degraded | E. Acetate produced (mg/l) |
|---|---|---|---|---|
| PFBA | 41.3 | 24.9 | 97 | 31.1 |
| PFOA | 44.4 | 29.5 | 97 | 23.9 |
| PFBS | 35.2 | 15.9 | 79 | 16.2 |
| PFOS | 39.2 | 18.0 | 71 | 10.0 |
| PFOSA | 18.5 | 6.1 | 51 | 4.7 |
| 6:2 FTS | 18.0 | 11.4 | 109 | 11.0 |
| 8:2 FTS | 23.5 | 6.9 | 48 | 5.1 |
| 6:2 FTOH | 19.4 | 7.1 | 55 | 6.6 |
| 8:2 FTOH | 25.1 | 17.5 | 100 | 15.0 |
| 8:2 diPAP | 16.2 | 1.8 | 17 | 2.1 |
| ADONA | 12.3 | 1.0 | 15 | 3.0 |

Controls included autoclaved vials prepared identical to the biological active vials, active vials without adding $NH_4^+$, and active vials seeded with *Geobacter sulfureducens* and added acetate to determine if iron reduction and buildup of Fe(II) might be responsible for the degradation (or removal via another mechanism) of these fluorinated compounds. Table III provides results for the incubations with initial concentrations of 100 mg/l, for the enrichment culture incubations. Similar results were obtained for the pure culture incubations, and incubations with initial concentrations of 0.1 mg/l, although $F^-$ analyses were more challenging and had larger errors for the lower concentrations. No decrease in the PFAS concentrations or buildup of $F^-$ was observed in any of the controls (including the active *Geobacter* controls). Table III shows a summary of results after 60 days of incubation. In all cases, acetate was produced, indicating an end product that do not contain fluorine. Column D shows the ratio of $F^-$ produced to $F^-$ expected if the decrease in concentration (column B) is the result of a complete defluorination, which seems to be the case for some of these compounds. Hence, it appears that A6 contains RDases and/or enzymes exhibiting reductive dehalogenase activity that can dehalogenate PFAAs (that do not contain C—H bonds), such as PFOA and PFOS in addition to select polyfluorinated PFAA precursors.

Interestingly, while during incubations of the pure A6 or the A6 enrichment culture in the absence of PFAS, the genes for the RDases are not expressed; they are expressed when PFAS are present and $F^-$ builds up.

A separate set of enrichment culture incubations to track PFOA and PFOS, including some intermediates, more carefully at different time points (Tables IV and V) were then conducted.

TABLE IV

Results of PFOA incubations vs. time, including intermediate and end products

| Day | PFOA (mM) | PFBA (mM) | PFPeA (mM) | PFHxA (mM) | PFHpA (mM) | $F^-$ (mM) | Acetate (mM) | $NH_4$ (mM) | Fe(II) (mM) |
|---|---|---|---|---|---|---|---|---|---|
| 0 | 0.247 | 0 | 0 | 0 | 0 | 0 | 0 | 3.32 | 0.032* |
| 7 | 0.214 | 0.0005 | 0 | 0.013 | 0.047 | 0.27 | 0.18 | 2.79 | 1.04 |
| 35 | 0.125 | 0.0051 | 0.0071 | 0.025 | 0.063 | 0.80 | 0.33 | 2.11 | 3.76 |
| 60 | 0.127 | 0.0069 | 0.0135 | 0.021 | 0.061 | 0.87 | 0.48 | 1.87 | 4.99 |

TABLE V

Results of PFOS incubations vs. time, including intermediate** and end products

| day | PFOS (mM) | PFBS (mM) | PFBA (mM) | PFPrA (mM) | $F^-$ (mM) | Acetate (mM) | $NH_4^+$ (mM) | Fe(II) (mM) | $SO_4^{2-}$ (mM) |
|---|---|---|---|---|---|---|---|---|---|
| 0 | 0.208 | 0 | 0 | 0 | 0 | 0 | 3.15 | 0.016* | 0.36* |
| 10 | 0.180 | 0 | 0.005 | 0.002 | 0.22 | 0.11 | 3.01 | 0.28 | 0.39 |
| 45 | 0.152 | 0.014 | 0.024 | 0.001 | 0.66 | 0.18 | 2.74 | 1.60 | 0.42 |
| 60 | 0.144 | 0.042 | 0.033 | 0.013 | 0.87 | 0.21 | 2.34 | 3.39 | 0.43 |

*initial concentrations in the growth medium.

$F^-$ was analyzed via IC on two different columns, each with two different eluents, and various gradients.

PFAS were analyzed via HPLC-MS with separate checks for selected PFAS by a different lab.

A total fluorine balance at each time point for both experiments is given in Table S2 VI and Table S3 VII for PFOA and PFOS respectively, accounting for the F in the initial compound, each intermediate, as well as $F^-$ ions produced. Results show a remarkable good fluorine balance for these experiments at each time point.

TABLE VI

Fluorine Balance for the PFOA degradation experiment with the A6 enrichment culture

| Time (days) | F in PFOA (mM) | F in PFBA (mM) | F in PFPeA (mM) | F in PFHxA (mM) | F in PFHpA (mM) | $F^-$ (mM) | Total F (mM) |
|---|---|---|---|---|---|---|---|
| 0 | 3.70 | 0 | 0 | 0 | 0 | 0 | 3.70 |
| 7 | 3.21 | 0.0005 | 0 | 0.013 | 0.05 | 0.27 | 4.16 |
| 35 | 1.88 | 0.005 | 0.007 | 0.025 | 0.06 | 0.80 | 3.73 |
| 60 | 1.91 | 0.007 | 0.014 | 0.021 | 0.06 | 0.87 | 3.85 |

TABLE VII

Fluorine balance for the PFOS degradation experiment with the A6 enrichment culture

| Time (days) | F in PFOS (mM) | F in PFBS (mM) | F in PFBA (mM) | F in PFPrA (mM) | $F^-$ (mM) | Total F |
|---|---|---|---|---|---|---|
| 0 | 3.54 | 0 | 0 | 0 | 0 | 3.53 |
| 10 | 3.06 | 0 | 0.04 | 0.009 | 0.22 | 3.33 |
| 45 | 2.58 | 0.13 | 0.17 | 0.005 | 0.66 | 3.54 |
| 60 | 2.45 | 0.38 | 0.23 | 0.07 | 0.87 | 4.00 |

Comparing Fe(II) production in incubations with and without PFOS and PFOA (Table VIII) shows that in the presence of these compounds, Fe(II) plus $F^-$ produced, is similar to Fe(II) produced in their absence, indicating that F is used as an electron acceptor by A6 instead of Fe(III) during the defluorination of these compounds.

TABLE VIII

Ratio of reduced electron acceptor to ammonium oxidized in the presence and absence of PFOS and PFOA

| day | Fe(II)/$NH_4^+$ | [Fe(II) + $F^-$]/$NH_4^+$ | Fe(II)/$NH_4^+$ |
|---|---|---|---|
| | with PFOS | with PFOS | control without PFOS |
| 10 | 1.91 | 3.50 | 4.53 |
| 45 | 3.85 | 5.47 | 5.65 |
| 60 | 4.19 | 5.28 | 5.78 |
| | with PFOA | with PFOA | control without PFOA |
| 7 | 1.89 | 2.40 | 3.02 |
| 35 | 3.07 | 3.73 | 4.31 |
| 60 | 3.42 | 4.02 | 5.34 |

The buildup of $F^-$, acetate, and sulfate for the case of PFOS indicates at least partial mineralization. The detection products such as PFBA suggests that desulfonation could be occurring, which may also explain the lack of detection of shorter-chained analogs of PFOS, such as perfluoroheptane sulfonate (PFHpS), perfluorohexane sulfonate (PFHxS), and perfluoropentane sulfonate (PFPeS).

The results of Examples 1 and 2 herein are notable given that the carbon-fluorine (C—F) bond is the strongest covalent bond in organic chemistry; hence perfluoroalkyl chemicals such as perfluorooctane sulfonate (PFOS) and carboxylic acid (PFOA) are very persistent in the environment, and defluorination of these compounds is exceeding difficult. Prior to the present application, it is believed that biodegradation (mineralization) of perfluoroalkyl chemicals has not been observed. Accordingly, the first ever biological method to defluorinate and mineralize per-fluorinated alkyl substances such as PFOA and PFOS via reductive dehalogenation is reported here, and that the same method also works to defluorinate and mineralize polyfluorinated alkyl substances.

Example 3—Fluorochemical Degradation

Hydrogen ($H_2$) was tested in two separate experiments, as an alternate electron donor to $NH_4^+$ for A6 to conduct PFAS degradation, specifically reductive defluorination. For this purpose, A6 was grown in both the solid and liquid inorganic Fe(III) medium (iFe) plus PFAS, with and without $NH_4^+$, but in the presence of $H_2$ in the headspace. Incubations were conducted with initial concentrations of either PFOA or PFOS of 100 mg/l.

The solid cultures were initially sparged with a $N_2/H_2$ gas mixture (described above) in an anaerobic glove bag. For the liquid cultures, 2 ml pure A6 culture was mixed with 8 mL of anoxic inorganic Fe(III) medium (iFe) plus 100 mg/l PFOA or PFOS, and with or without $NH_4^+$ in a 50 ml serum bottles. The headspace of each incubation vial was vacuumed and then flushed with a $N_2/H_2$ (80:20) mixture. The serum vials were then placed on a rotary shaker at 150 rpm at 30° C. for 35-day incubations. A total of 4 sets was included in the liquid cultures incubations:
1) A6+PFOA/PFOS+Fe(III)+$NH_4^+$ (labeled "without $H_2$);
2) A6+PFOA/PFOS+Fe(III)+$H_2$ (labeled with H2); 3) A6+PFOA/PFOS+$H_2$; 4) autoclaved A6+PFOA/PFOS+Fe(III)+$H_2$.

For each incubation, three subsamples were collected destructively. Samples were collected on day 0, 7, 21 and 30 for Fe(II), $NH_4^+$, $F^-$ and PFOA/PFOS analyses.
Results 1. Effect of $H_2$ on Growth of A6 with PFOA/PFOS in Solid Media Feammox Acidimicrobiaceae sp. A6 colonies were found to be growing without $NH_4^+$ in agar (10 g/L) ferric medium plates (iFeo) after 21 days in the presence of $H_2$, with and without PFAS. The control samples in the same agar iFeo medium plate but under $H_2$-free conditions did not exhibit any growth of A6. A slow growth of A6 colonies was also found in agar plates incubated in the presence of $H_2$, but without Fe (III) and $NH_4^+$. Indicating that A6 could grow with these PFAS as the sole electron acceptor.

The presence of fluoride was detected in these plates showing that these PFAS were being defluorinated in the solid medium.

Figure 5:
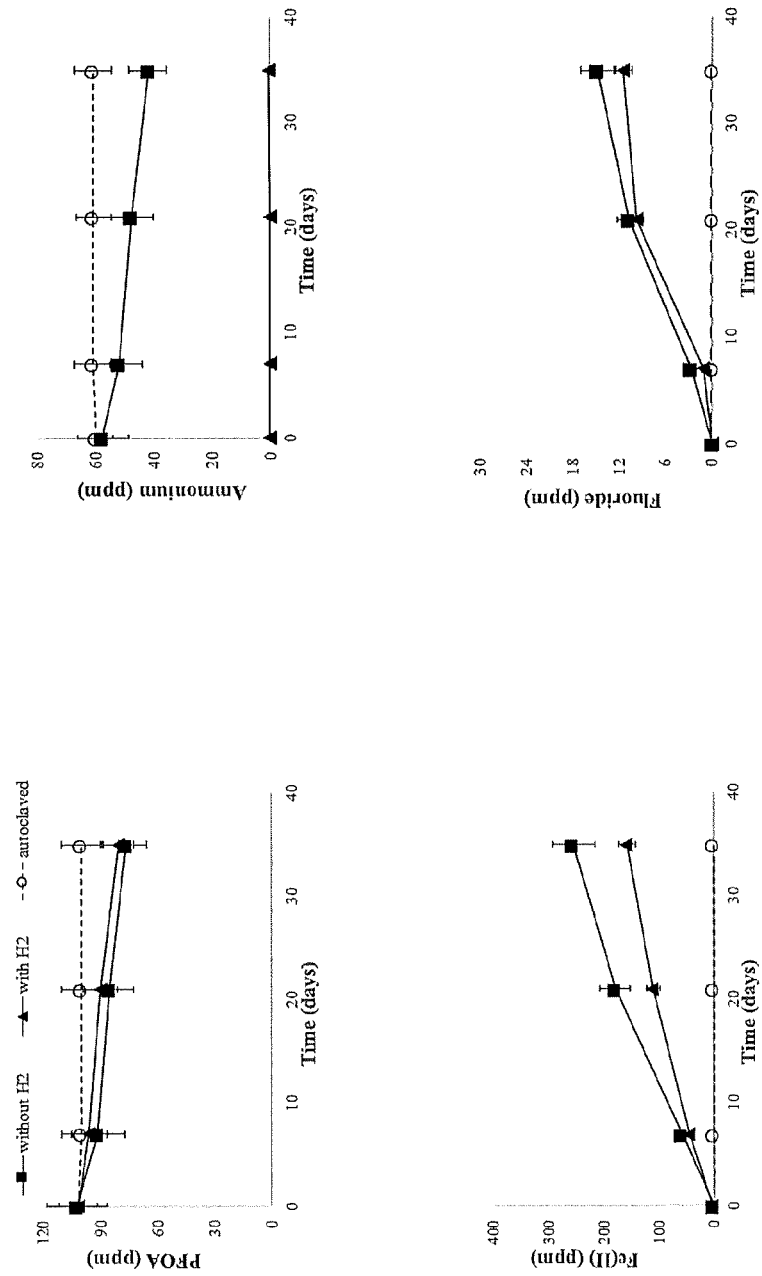
FIG. 5 illustrates results from PFOA incubations with either ammonium or hydrogen according to some embodiments.
Figure 6:
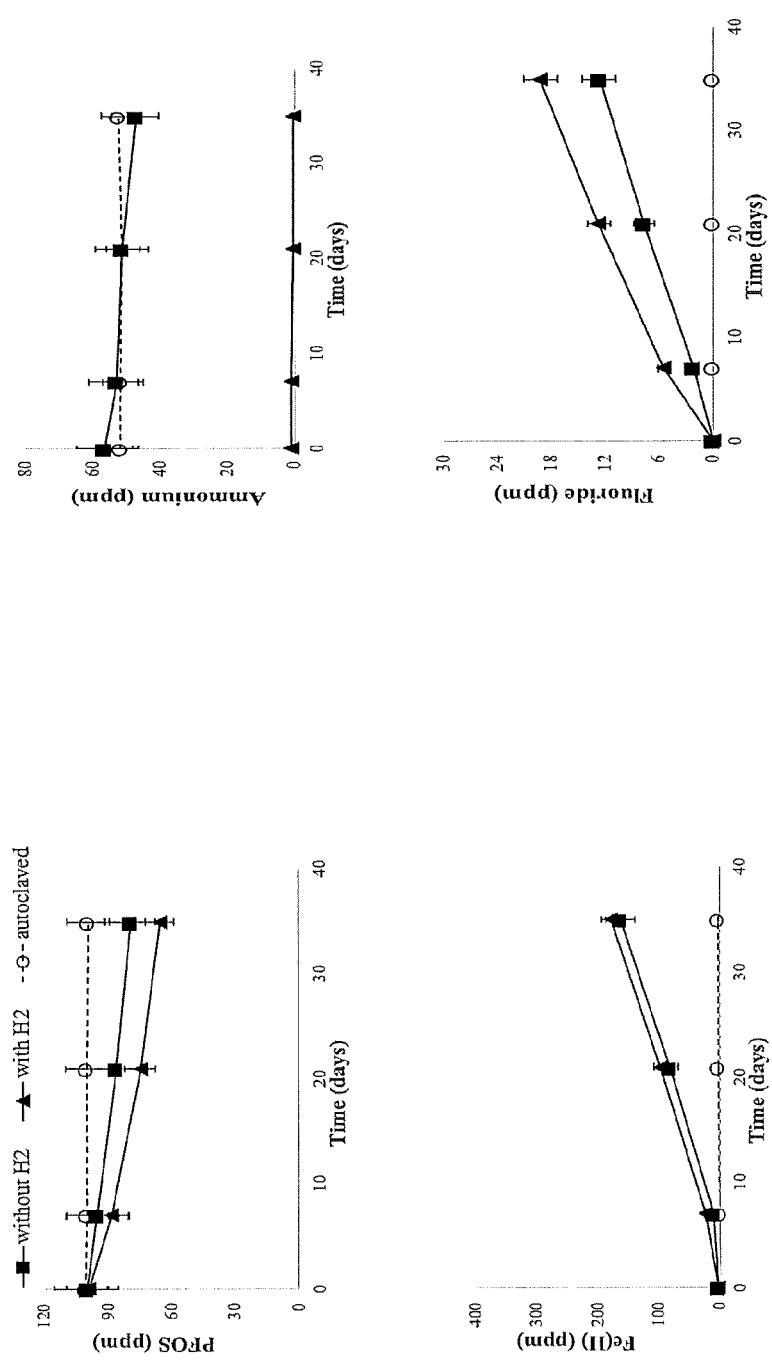
FIG. 6 illustrates results from Perfluorooctane sulfonate (PFOS) incubations with either ammonium or hydrogen according to some embodiments.

FIG. 5 illustrates the results of the PFOA incubations (100 mg/l) with either $NH_4^+$ or $H_2$ as electron donor. FIG. 6 illustrates the results of the PFOS incubations (100 mg/l) with either $NH_4^+$ or $H_2$ as electron donor. As provided in FIGS. 5 and 6, fluorochemical degradation proceed in both:

A. The presence of $H_2$ and the absence of $NH_4^+$
B. The presence of $NH_4^+$ and the absence of $H_2$ As described hereinabove, it is also contemplated that $NH_4^+$ and $H_2$ can both be present in the same medium or system to effectuate fluorochemical degradation.

2. Gene Expression During Defluorination with $NH_4^+$ or $H_2$ as Electron Donor Expression of the same dehalogenase genes or dehalogenase related genes (Fac-1: fluoroacetate dehalogenase related gene, and rdhA: dehalogenase gene), reported previously when defluorination was observed with $NH_4^+$ as electron donor, was also observed when $H_2$ is the electron donor and PFAS are present with $F^-$ being produced.

3. Conclusion

These results show that in addition to $NH_4^+$, $H_2$ can be used as electron donor for the reductive defluorination of PFAS by the pure A6 or A6 enrichment culture. $H_2$ can be either supplied directly or indirectly by supplying a fermentable organic substrate which results in the production of $H_2$.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

---

SEQUENCE LISTING

The patent contains a lengthy sequence listing. A copy of the sequence listing is available in electronic form from the USPTO web site (https://seqdata.uspto.gov/?pageRequest=docDetail&DocID=US12252423B2). An electronic copy of the sequence listing will also be available from the USPTO upon request and payment of the fee set forth in 37 CFR 1.19(b)(3).

---

The invention claimed is:

1. A medium comprising:
an electron donor; a fluorochemical component; an electron acceptor; and a Feammox bacterium and/or one or more enzymes exhibiting reductive dehalogenase activity capable of fluorochemical degradation in conjunction with oxidation of the electron donor and electron transfer to the electron acceptor.

2. The medium of claim 1, wherein the electron acceptor is fluorine resulting in the production of fluoride.

3. The medium of claim 2, wherein the fluorine is derived from the fluorochemical component.

4. The medium of claim 1, wherein the electron donor comprises molecular hydrogen ($H_2$).

5. The medium of claim 1, wherein the electron donor comprises ammonium or an organic compound.

6. The medium of claim 1, wherein the electron donor comprises a mixture of $H_2$ and ammonium.

7. The medium of claim 1, wherein the one or more enzymes are present in the medium and have an amino acid sequence comprising at least 60% identity of a sequence selected from SEQ ID NOS: 50-53.

8. The medium of claim 7, wherein the one or more enzymes have an amino acid sequence selected from SEQ ID NOS: 50-53.

9. The medium of claim 1, wherein the one or more enzymes are expressed by a bacterium in the medium.

10. The medium of claim 1, wherein the electron acceptor is a mixture of metal and fluorine.

11. The medium of claim 1, wherein the fluorochemical component comprises one or more fluorochemicals.

12. The medium of claim 11, wherein the fluorochemical component comprises perfluoroalkyl compounds.

13. The medium of claim 11, wherein the fluorochemical component comprises a fluorinated carboxylic acid.

14. The medium of claim 11, wherein the fluorochemical component comprises a fluorinated alcohol.

15. The medium of claim 11, wherein the fluorochemical component comprises a fluorinated sulfonate.

16. The medium of claim 1, wherein the medium further comprises water.

17. The medium of claim 1, wherein the medium further comprises soil, sludge, sorbent or solid contaminated with the fluorochemical component.

18. A system comprising:
a reactor, the reactor comprising a medium including an electron donor; a fluorochemical component; an electron acceptor; and a Feammox bacterium and/or one or more enzymes exhibiting reductive dehalogenase activity capable of fluorochemical degradation in conjunction with oxidation of the electron donor and electron transfer to the electron acceptor.

19. The system of claim 18, wherein the electron acceptor is fluorine resulting in the production of fluoride.

20. The system of claim 19, wherein the fluorine is derived from the fluorochemical component.

21. The system of claim 18, wherein the electron donor comprises molecular hydrogen ($H_2$).

22. The system of claim 18, wherein the electron donor comprises ammonium or an organic compound.

23. The system of claim 18, wherein the electron donor comprises a mixture of $H_2$ and ammonium.

24. The system of claim 18, wherein the electron acceptor is an anode.

25. The system of claim 24, wherein the Feammox bacterium colonizes the anode.

26. The system of claim 18, wherein the one or more enzymes are present in the medium and have an amino acid sequence comprising at least 60% identity of a sequence selected from SEQ ID NOS: 50-53.

* * * * *